United States Patent [19]

Nohara et al.

[11] Patent Number: 4,738,975

[45] Date of Patent: Apr. 19, 1988

[54] PYRIDINE DERIVATIVES, AND USE AS ANTI-ULCER AGENTS

[75] Inventors: Akira Nohara; Yoshitaka Maki, both of Kyoto, Japan

[73] Assignee: Takeda Chemical Industries, Ltd., Osaka, Japan

[21] Appl. No.: 875,702

[22] Filed: Jun. 18, 1986

[30] Foreign Application Priority Data

Jul. 2, 1985 [JP] Japan ................... 60-146395
Jul. 19, 1985 [JP] Japan ................... 60-160457

[51] Int. Cl.$^4$ ............... A61K 31/415; C07D 401/06; C07D 401/12
[52] U.S. Cl. ...................... 514/338; 546/271
[58] Field of Search ............... 546/271; 514/338

[56] References Cited

U.S. PATENT DOCUMENTS

| | | | |
|---|---|---|---|
| 4,045,563 | 8/1977 | Berntsson et al. | 546/271 |
| 4,255,431 | 3/1981 | Junggren et al. | 546/271 |
| 4,472,409 | 9/1984 | Senn-Bilfinger | 546/271 |

FOREIGN PATENT DOCUMENTS

| | | | |
|---|---|---|---|
| 5129 | 3/1979 | European Pat. Off. | 546/271 |
| 45200 | 7/1981 | European Pat. Off. | 546/271 |
| 74341 | 8/1982 | European Pat. Off. | 546/271 |
| 134400 | 5/1984 | European Pat. Off. | 546/271 |
| 2134523 | 8/1984 | United Kingdom | 546/271 |

OTHER PUBLICATIONS

European Patent Publication Nos. 166,287 and 167,943, (Basic Abstracts Journal).
Australian Patent Publication No. 8,435,643, (Basic Abs. Journal).

Primary Examiner—Henry R. Jiles
Assistant Examiner—J. Richter
Attorney, Agent, or Firm—Wegner & Bretschneider

[57] ABSTRACT

The compound of the formula

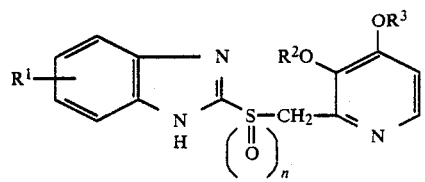

wherein $R^1$ is hydrogen, fluorine, methoxy or trifluoromethyl, $R^2$ is a $C_{1-8}$ alkyl, $R^3$ is a $C_{1-8}$ alkyl which may be fluorinated, and n is 0 or 1, or a pharmacologically acceptable salt thereof is useful for prevention and treatment of digestive ulcers (e.g. gastric ulcer, duodenal ulcer) and gastritis.

36 Claims, No Drawings

PYRIDINE DERIVATIVES, AND USE AS ANTI-ULCER AGENTS

This invention relates to pyridine derivatives which are useful as anti-ulcer agents, their production and use.

As pyridine derivatives having anti-ulcer action, those described in Japanese Unexamined Patent Laid-open No. 141783/1979, and those described in Japanese Unexamined Laid-open No. 135881/1983 are known.

However, the known compounds described above are not necessarily considered desirable anti-ulcer agents because of their poor gastric mucosa-protecting action though they inhibit secretion of gastric juice. Moreover they have a physical defect in that they are unstable and easily decomposed. Thus those agents that not only inhibit secretion of gastric juice but also protect the gastric mucosa more effective have been desired.

As the result of the inventors' research to obtain anti-ulcer agents which are able to inhibit effectively secretion of gastric juice, to protect the gastric mucosa, to exert excellent anti-ulcer action, etc., the inventors found that some pyridine derivatives are suitable for the purpose and completed this invention after their further research.

This invention relates to (1) Pyridine derivatives of the formula (I), or the salts thereof

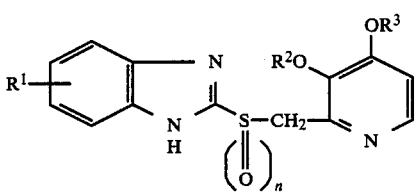
(I)

wherein $R^1$ is hydrogen, fluorine, methoxy or trifluoromethyl, $R^2$ is a lower alkyl, $R^3$ is a lower alkyl which may be fluorinated, and n is 0 or 1, (2) A method for producing pyridine derivatives of the formula (I), or the salts thereof, which comprises allowing a compound of the formula (II)

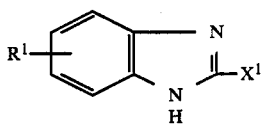
(II)

to react with a compund of the formula (III)

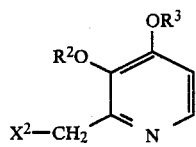
(III)

wherein $R^1$, $R^2$ and $R^3$ are the same as defined above, and either one of $X^1$ and $X^2$ is SH and the other is a leaving group, followed by oxidation, if necessary, and (3) A pharmaceutical composition for preventing or treating digestive ulcers, which contains an effective amount of pyridine derivatives of the formula (I) or a pharmacologically acceptable salt thereof, and carriers.

The leaving groups $X^1$ and $X^2$ in the compounds of the formula (II) and (III) are exemplified by halogens, preferably chlorine, bromine and iodine, hydroxyl groups activated by esterification, such as arylsulfonyloxy groups, i.e. organic sulfonic acid residues (e.g. p-toluenesulfonyloxy group, benzenesulfonyloxy group), alkylsulfonyloxy groups having 1 to 4 carbons each (e.g. methanesulfonyloxy group), and organic phosphoric acid residues such as diphenylphosphoryloxy group, dibenzylphosphoryloxy group and dialkylphosphoryloxy groups having 1 to 4 carbons each (e.g. dimethylphosphoryloxy group).

The lower alkyl groups represented by $R^2$ in the formulas above are preferably lower alkyl groups having 1 to 8 carbon atoms each such as methyl, ethyl, propyl, isopropyl, butyl, isobutyl, pentyl, hexyl, heptyl, and octyl, among which lower alkyl groups having 1 to 4 carbon atoms each are more preferable.

The lower alkyl groups, which may be fluorinated by 1 to 8 fluorine atoms, represented by $R^3$, are those having 1 to 8 carbon atoms each, preferably the alkyl groups specifically written above for $R^2$. Fluorinated lower alkyl groups are exemplified by 2,2,2-trifluoroethyl, 2,2,3,3,3-pentafluoropropyl, 1-(trifluoromethyl)-2,2,2-trifluoroethyl, 2,2,3,3-tetrafluoropropyl, 2,2,3,3,4,4,4-heptafluorobutyl, and 2,2,3,3,4,4,5,5-octafluoropentyl, among which fluorinated lower alkyl groups having 2 to 4 carbon atoms each are preferable.

$R^1$ is attached at the position 4 or 5, preferably at the position 5.

The desired, sulfide derivatives (I) (n=0), can be produced by allowing the compound (II) to react with the compound (III).

The reaction is allowed to proceed preferably in the presence of a base. Such bases include hydrides of alkali metals, such as sodium hydride and potassium hydride, alkali metals such as metallic sodium, sodium alcoholates such as sodium methoxide and sodium ethoxide, carbonates of alkali metals such as potassium carbonate and sodium carbonate, and organic amines such as triethylamine. Solvents used for the reaction include alcohols such as methanol and ethanol, and dimethylformamide. The amount of the base used for the reaction described above is usually slightly more than one equivalent, but large excess of the base may be used. That is, about one to 10 equivalents, more preferably about one to 4 equivalents of the base are used. The reaction temperature usually ranges from 0° C. up to about the boiling point of the solvent used, preferably about 20° to 80° C. The reaction time is about 0.2 to 24 hours, preferably about 0.5 to 2 hours.

The desired, sulfinyl derivatives (I) (n=1), can be produced by oxidation of a compound (I) (n=0). The oxidants used for this reaction include peracids such as metachloroperbenzoic acid, peracetic acid, trifluoroperacetic acid, and permaleic acid, hydrogen peroxide, sodium bromite, and sodium hydrochlorite. The solvents used for the reaction include halogenated hydrocarbons such as chloroform and dichloromethane, ethers such as tetrahydrofuran and dioxane, amides such as dimethylformamide, alcohols such as ethanol, isopropanol, and t-butanol, and water, each of which may be use alone or in mixture. Catalysts such as vanadium pentaoxide and tungstic acid can be used in some cases. Preferable amount of the said oxidants is about one equivalent or slight excess for the compound (I) (n=0). That is, about 1 to 3 equivalents, more preferably, about one to 1.5 equivalents of the oxidant is used.

The reaction temperature ranges from the temperature under ice-cooling to the boiling point of the solvent used, usually from the temperature under ice-cooling to the room temperature, more preferably from about 0 to 10° C. The reaction time is usually about 0.1 to 24 hours, more preferably about 0.1 to 4 hours.

A salt of a compound (I) of n=0 is stable, and an acid salt of a compound (I) of n=1 can exist though unstable in its aqueous solution.

In the following, production of a compound from a starting compound (III) wherein $X^2$ is a leaving group is described.

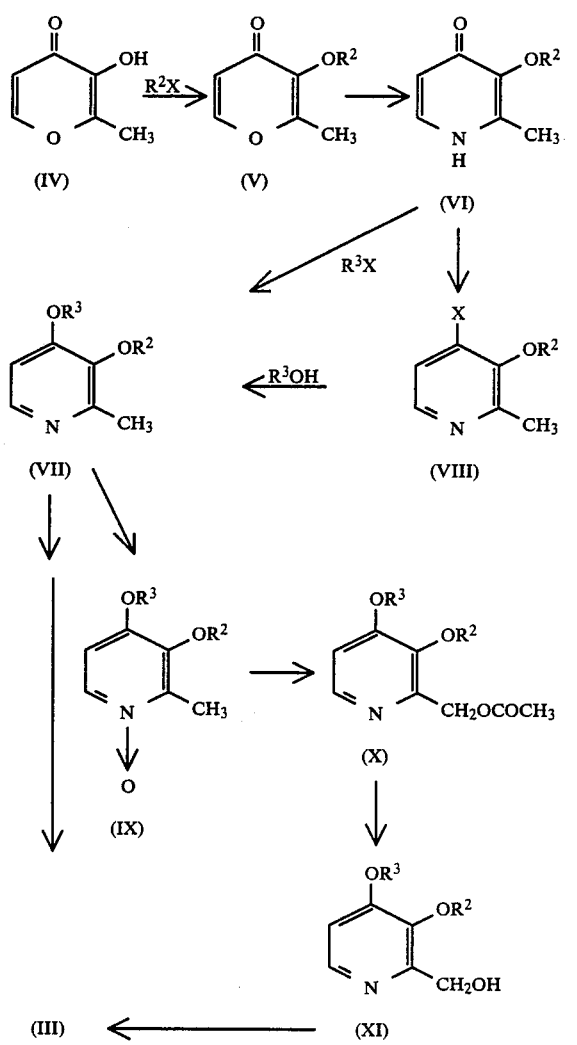

Reaction of maltol (IV) with an alkyl halide represented by $R^2X$ in the presence of silver oxide etc. gives the compound (V), which is allowed to react with ammonia water, to give a pyridone derivative (VI). The compound (VI) is converted into a compound (VII) by direct alkylation with alkyl halide, or converted into a halogen derivative (VIII) by a halogenating reagent such as phosphorus oxychloride, followed by the reaction with a lower alcohol represented by $R^3OH$ in the presence of a base, to give a command (VII). Then the compound (VII) is either directly halogenated into a compound (III) with N-bromosuccinimide or with chlorine, or converted into a compound (IX) with an oxidant such as m-chloroperbenzoic acid, followed by the reaction with acetic anhydride to give a compound (X) which is then hydrolyzed to give a compound (XI), which is converted into a compound (III) with a halogenating reagent such as thionyl chloride.

The alkyl halides used for the production of the compound (V) and the compound (VII) include methyl iodide, ethyl iodide, propyl iodide, isopropyl iodide, butyl iodide, pentyl iodide, and hexyl iodide, about 1 to 10 equivalents of each of which is used. The bases include silver oxide, potassium carbonate and sodium carbonate, and the solvents include dimethylformamide and dimethylacetamide. The reaction is allowed to proceed usually at the room temperature.

Halogenating reagents used for the production of the compound (VIII) include phosphorus oxychloride, phosphorus pentachloride and phosphorus tribromide, an equivalent to large excess each of which is used. The reaction temperature is about 50°–150° C. Alcohols used for the reaction from the compound (VIII) to the compound (VII) include methanol, ethanol, propanol, isopropanol, butanol, pentanol, hexanol, 2,2,2-trifluoroethanol, 2,2,3,3,3-pentafluoropropanol, 2,2,3,3,-tetrafluoropropanol, 1-(trifluoromethyl)-2,2,2-trifluoroethanol, 2,2,3,3,4,4,4-heptafluorobutanol, and 2,2,3,3,4,4,5,5-octafluoropentanol, an equivalent to large excess of each of which is used. Bases used include sodium or potassium alcoholate of each of the alcohols, potassium t-butoxide, and sodium hydride. The suitable reaction temperature is chosen in the range from the room temperature to the boiling point of the alcohol used.

Direct bromination of the compound (VII) with N-bromosuccinimide is desirably performed under irradiation in a solvent such as carbon tetrachloride, chloroform, and tetrachloroethane.

Oxidants used for the reaction from the compound (VII) to the compound (IX) include peracids such as methachloroperbenzoic acid, peracetic acid, trifluoroperacetic acid, and permaleic acid, and hydrogen peroxide. Solvents used for the reaction include halogenated hydrocarbons such as chloroform, and dichloromethane, ethers such as tetrahydrofuran and dioxane, amides such as dimethylformamide, acetic acid or water, each of which is used alone or in mixture. The suitable amount of the oxidants is an equivalent to an excess for the compound (VII), preferably about 1 to 10 equivalents. The reaction temperature ranges from the temperature under ice-cooling to about the boiling point of the solvent used. The reaction time ranges usually from about 0.1 to 24 hours, more preferably from about 0.1 to 4 hours.

The production of the compound (X) from the compound (IX) is performed by heating the compound (IX) in the presence of acetic anhydride alone or together with a mineral acid such as sulfuric acid and perchloric acid (at about 80° to 120° C.). The reaction time is usually 0.1 to 10 hours.

The compound (XI) can be obtained by alkali hydrolysis of the compound (X), and alkalis used here include sodium hydroxide, potassium hydroxide, potassium carbonate, and sodium carbonate. Solvents used include methanol, ethanol, and water. The reaction temperature ranges usually from about 20° to 60° C., and the reaction time ranges from about 0.1 to 2 hours.

The production of the compound (III) from the compound (XI) is performed by using a chlorinating reagent such as thionyl chloride, an acid chloride of an organic sulfonic acid or of an organic phosphoric acid, such as methanesulfonyl chloride, p-toluenesulfonyl chloride, and diphenylphosphoryl chloride. When a chlorinating reagent such as thionyl chloride is used, an equivalent to a large excess of the chlorinating reagent is used for the amount of the compound (XI). The solvents used include chloroform, dichloromethane, and tetrachloroethane. The reaction temperature ranges usually from about 20° to 80° C., and the reaction time ranges from about 0.1 to 2 hours. When an acid chloride of an organic sulfonic acid or of an organic phosphoric acid is used, an equivalent to a small excess of the chloride is used for the amount of the compound (XI) usually in the presence of a base. Such bases include organic bases such as triethylamine and tributylamine, and inorganic bases such as sodium carbonate, potassium carbonate and sodium hydrogen carbonate, an equivalent to a small excess of each of which is used. The solvents used include chloroform, dichloromethane, carbon tetrachloride, and acetonitrile. Suitable reaction temperature and reaction time are chosen in the range from the temperature under ice-cooling to about the boiling point, and in the range from a few minutes to a few hours, respectively.

The compound (I) can be produced according to, for example, the method of production disclosed under Japanese Unexamined Patent Laid-open No. 192880/1983. That is, a compound of the formula

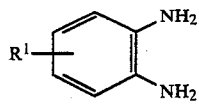

wherein $R^1$ is the same as defined above, is allowed to react with a compound of the formula

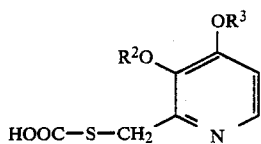

wherein $R^2$ and $R^3$ are the same as defined above, followed by oxidation if necessary, or a compound of the formula

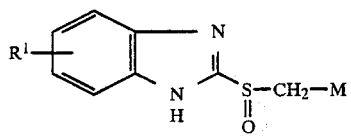

wherein $R^1$ is the same as defined above, M is K, Na or Li is allowed to react with a compound of the general formula

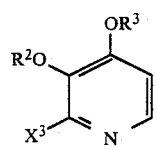

wherein $R^2$ and $R^3$ are the same as defined above, and $X^3$ is the same as the leaving group represented by $X^1$ or $X^2$.

The desired compound (I) produced by the reactions described above can be isolated and purified with usual procedures such as recrystallization and chromatography.

The compounds (I) of this invention may be converted into salts which are pharmacologically acceptable, with a usual method. Such salts include hydrochloride, hydrobromide, hydroiodide, phosphate, nitrate, sulfate, acetate, citrate, and sodium, potassium, magnesium, and calcium salts.

Pharmacological actions of the compounds of the present invention are described as follows.

While the role of acid in causing gastric and duodenal ulcerations has been well known, importance of the protecting ability of gastric mucosa has been attracting the attention in recent years.

Miller T. A., Am. J. Physiol., 245, G601 (1983)

As a method of determining the ability to protect gastric mucosa, gastric mocosal injury induced by ethanol [Robert A., Gastroenterology 77, 761 (1979)] is often used. This method was applied to evaluation of the compounds of this invention.

EXPERIMENTAL METHOD

Male Sprague-Dawley rats 7-weeks old were fasted for 24 hours. These animals were administered test compounds into the stomach by using a gastric tube. After 30 minutes, 1 ml of 100% ethanol was administered orally. The animals were killed by carbon dioxide gas 60 minutes after ethanol administration. The stomach was removed together with the lower part of esophagus and the duodenum. The esophagus was clipped, 10 ml of 1% formalin solution was instilled into the stomach from the duodenum, and then the duodenum was clipped. The whole stomach was immersed in 1% formalin solution. About 15 minutes later, the stomachs were opened along the greater curvature. Length of the lesions which occurred in the gastric corpus mucosa was measured under a dissecting microscope with a square-grid eye piece (×10). The sum total length of the individual lesions in each animal was measured, and the average value per group was calculated. Based on the difference between the average value of each group and that of the control group, the inhibition rate was determined. The test compound was suspended in a 5% gum arabic solution, and administered in a volume of 2 ml/kg.

EXPERIMENTAL RESULTS

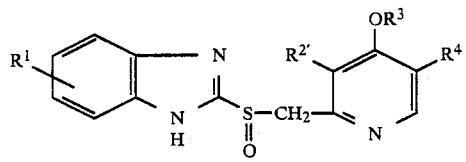

| $R^1$ | $R^{2'}$ | $R^3$ | $R^4$ | Action of protecting gastric mucosa[a] $ID_{50}$ (mg/kg, p.o.) |
|---|---|---|---|---|
| H | OCH$_3$ | CH$_3$ | H | 3.2 |
| 5-CF$_3$ | OCH$_3$ | CH$_3$ | H | 3.0 |
| H | OCH$_3$ | CH$_2$CF$_3$ | H | 6.2 |
| 5-OCH$_3$ | CH$_3$ | CH$_3$ | CH$_3$*[1] | 22.0 |

-continued

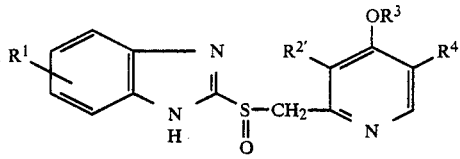

| R¹ | R²′ | R³ | R⁴ | Action of protecting gastric mucosa[a] ID$_{50}$ (mg/kg, p.o.) |
|---|---|---|---|---|
| 5-CF$_3$ | CH$_3$ | CH$_3$ | H*[2] | 24.0 |

*[1]The compound disclosed in Example 23 of U.S. Pat. No. 4,255,431 (Japanese Unexamined Patent Laid-open No. 141783/1979)
*[2]The compound disclosed in Example 3 of U.S. Pat. No. 4,472,409 (Japanese Unexamined Patent Laid-open No. 135881/1983)
[a]Using 6 rats per group, each of the test compounds was administered in a dose of 3, 10 and 30 mg/kg to determine ID$_{50}$.

As shown by the above data, the compounds of this invention have an evidently superior action in protecting the gastric mucosa as compared with known compounds. Besides, the compound (I) of this invention shows excellent actions of inhibiting gastric juice secretion, protecting gastric mucosa and preventing ulceration.

Regarding the toxicity of the compound (I) of this invention, oral administration of the compound employed for the experiment of an action protecting gastric mucosa (the compounds of $R^1=H$, $R^2=CH_3$, $R^3=CH_3$, and of $R^1=H$, $R^2=CH_3$, $R^3=CH_2CF_3$) to mice even in a dose of 500 mg/kg caused no fatal effect, thus the compound (I) generally is low in toxicity.

As described in the foregoing, the compounds (I) of this invention have excellent gastric juice-secretion-inhibiting activity, gastric mucosa-protecting activity, and anti-ulcer activity, and can be used for the prevention and treatment of digestive ulcers (e.g. gastric ulcer, duodenal ulcer) and gastritis in mammals (e.g. mouse, rat, rabbit, dog, cat, man) and because of the low toxicity.

For the treatment of digestive ulcer in mammals, the compounds (I) of this invention can be orally given in the dosage form such as capsules, tablets and granules obtained by mixing with pharmacologically acceptable carriers, such as excipients (e.g. lactose, starch, sucrose, etc.), disintegrators (e.g. starch, carboxymethyl-cellulose calcium, etc.), lubricants (e.g. magnesium stearate, talc, etc.), binders (e.g. hydroxypropyl-cellulose, hydroxypropylmethylcellulose, macrogol, etc.), and so on. The dose ranges from about 0.01 to 30 mg/kg/day, more preferably from about 0.1 to 3 mg/kg/day.

The compound with n=0 among the compounds (I) of this invention are useful starting compounds for the production of the compounds with n=1.

The compounds (I) of this invention have not only gastric juice secretion-inhibiting-activity but also gastric mucosa-protecting-activity, and therefore they exert remarkable anti-ulcer action. Thus the compounds (I) of this invention are useful for prevention and treatment of gastric ulcer, duodenal ulcer, gastritis, etc.

The production of the starting compounds used for this invention and the compounds (I) of this invention are illustrated in detail in the following Reference Examples and Examples.

REFERENCE EXAMPLE 1

3-Methoxy-2-methyl-4(1H)-pyridone(1.39 g) and propyl iodide (2.0 ml) were dissolved in dimethylformamide (20 ml), to which silver oxide (2.31 g) was added in small portions and stirred vigorously at room temperature for 5 hours. The reaction mixture was diluted with chloroform (100 ml), washed with water, dried and evaporated. The residue was purified by flash chromatography (chloroform) on silica gel, to give 3-methoxy-2-methyl-4-propoxypyridine (1.7 g) as a light brown oil.

NMR(CDCl$_3$) δ: 1.06(3H, t, J=7 Hz), 1.86(2H, m), 2.45(3H, s), 3.81(3H, s), 3.96(2H, t, J=7 Hz), 6.66(1H, d, J=6 Hz), 8.06(1H, d, J=6 Hz).

REFERENCE EXAMPLE 2

3-Methoxy-2-methyl-4(1H)-pyridone (5.6 g) was suspended in phosphorus oxychloride (50 ml), refluxed for 10 hours, and concentrated. To the resultant residue was added toluene and the residual phosphorus oxychloride was evaporated under reduced pressure. To the resultant oily substance were added chloroform and water and the chloroform layer was separated. The aqueous layer was made alkaline with potassium carbonate and extracted with chloroform. The chloroform solutions thus obtained were combined, washed with water, dried, and evaporated. The residue was purified by column chromatography on silica gel, to give 4-chloro-3-methoxy-2-methylpyridine (4.8 g) as a light brown oil.

NMR(CDCl$_3$) δ: 2.53(3H, s), 3.84(3H, s), 7.14(1H, d, J=6 Hz), 8.12(1H, d, J=6 Hz).

REFERENCE EXAMPLE 3

To a solution of 4-chloro-3-methoxy-2-methylpyridine (3.2 g) in methanol (5 ml) was added dropwise under ice-cooling a solution of 28% sodium methylate in methanol (20 ml) and the mixture, refluxed for 10 hours, and concentrated to dryness. To the residue, were added ice-water (10 ml) and then chloroform (100 ml) in this order, and the chloroform layer was separated, washed with water, dried, and evaporated. The residue was purified by column chromatography on silica gel, to give 3,4-dimethoxy-2-methylpyridine (2.95 g) as a light brown oil.

NMR(CDCl$_3$) δ: 2.46(3H, s), 3.79(3H, s), 3.86(3H, s), 6.18(1H, d, J=6 Hz), 8.11(1H, d, J=6 Hz).

REFERENCE EXAMPLE 4

4-Chloro-3-methoxy-2-methylpyridine (3.14 g) was added to a solution of sodium (2.0 g) in ethanol (30 ml), and the solution was refluxed by heating for 10 hours. The solvent was evaporated and the residue was added to ice water, which was extracted with chloroform, washed with water, dried and evaporated. The residue was purified by column chromatography on silica gel, to give 4-ethoxy-3-methoxy-2-methyl-pyridine (2.6 g) as a light brown oil.

NMR(CDCl$_3$) δ: 1.45(3H, t, J=8 Hz), 2.46(3H, s), 3.81(3H, s), 4.10(2H, q, J=8 Hz), 6.66(1H, d, J=5 Hz), 8.06(1H, d, J=5 Hz).

REFERENCE EXAMPLE 5

To a solution of 3-methoxy-2-methyl-4-propoxypyridine (1.0 g) in carbon tetrachloride (70 ml), was added N-bromosuccinimide (1.0 g) and the mixture was irradiated with and infrared lamp (Toshiba, 100 V, 375 WR) for 2 hours at reflux. An insoluble substance was filtered off, and the filtrate was concentrated and purified by column chromatography on silica gel, to give 2-bromomethyl-3-methoxy-4-propoxypyridine (0.4 g) as a reddish brown oil.

NMR(CDCl$_3$) δ: 1.06(3H, t, J=7 Hz), 1.87(2H, m), 3.98(3H, s), 4.01(2H, t, J=7 Hz), 4.58(2H, s), 6.77(1H, d, J=6 Hz), 8.16(1H, d, J=6 Hz).

REFERENCE EXAMPLE 6

(a) In a similar manner to Reference Example 5, 2-bromomethyl-3,4-dimethoxypyridine was produced from 3,4-dimethoxy-2-methylpyridine. The product was a reddish brown oil.

(b) Similarly, 2-bromomethyl-4-ethoxy-3-methoxypridine was produced from 4-ethoxy-3-methoxy-2-methylpyridine. The product was a reddish brown oil.

REFERENCE EXAMPLE 7

A mixture of 4-chloro-3-methoxy-2-methylpyridine (7.8 g), 2,2,2-trifluoroethanol (24.7 g) and potassium t-butoxide (27.76 g) was heated at 110° C. for 18 hours, then concentrated, diluted with water, and extracted twice with chloroform. The extract was dried, from which chloroform was evaporated, and the residue was purified by column chromatography on silica gel (chloroform-methanol (400:9)), to give 3-methoxy-2-methyl-4-(2,2,2-trifluoroethoxy)pyridine (5.12 g) as a white or pale yellow solid.

NMR(CDCl$_3$) δ: 2.49(3H, s), 3.84(3H, s), 4.42(2H, q, J=8 Hz), 6.67(1H, d, J=5.5 Hz), 8.14(1H, d, J=5.5 Hz).

REFERENCE EXAMPLE 8

To 2,2,3,3,3-pentafluoropropanol (21 ml) were added in small portions, potassium tert-butoxide (23.6 g) and then 4-chloro-3-methoxy-2-methyl-pyridine (7.5 g). After being refluxed for 40 hours, the reaction mixture was cooled, to which ethyl acetate was added and the insoluble substance was filtered off. The filtrate was concentrated and purified by column chromatography, to give 3-methoxy-2-methyl-4-(2,2,3,3,3-pentafluoropropoxy)pyridine (1.7 g) as a light yellow oil while 4.1 g of the starting material was recovered at the same time.

NMR(CDCl$_3$) δ: 2.48(3H, s), 3.81(3H, s), 4.49(2H, t, J=12 Hz), 6.67(1H, d, J=5.5 Hz), 8.14(1H, d, J=5.5 Hz).

EXAMPLE 1

To a mixture of potassium salt of 2-mercaptobenzimidazole (1.45 g), potassium carbonate (1.0 g) and dimethylformamide (10 ml) was added dropwise with stirring a solution of 2-bromomethyl-3,4-dimethoxypyridine (1.18 g) in dimethylformamide (2 ml), and the mixture was stirred at room temperature for 30 minutes, to which chloroform (100 ml) was added. The reaction mixture was washed with water, 1N-sodium hydroxide and water in this order, dried (with sodium sulfate) and evaporated. The residue was purified by column chromatography on silica gel (chloroform-methanol (50:1)), to give 2-[(3,4-dimethoxypyrid-2-yl)methylthio]benzimidazole (1.08 g) as a light yellow oil.

NMR(CDCl$_3$) δ: 3.80(3H, s), 3.82(3H, s), 4.43(2H, s), 6.70(1H, d, J=6 Hz), 7.0–7.2(2H, m), 7.4–7.6(2H, m), 8.13(1H, d, J=6 Hz).

EXAMPLE 2

To a solution of potassium salt of 2-mercaptobenzimidazole (0.4 g) in dimethylformamide (5 ml), was added dropwise a solution of 2-bromomethyl-3-methoxy-4-propoxypyridine (0.4 g) in dimethylformamide, and stirred at room temperature for 1 hour. The reaction mixture was diluted with chloroform (50 ml), washed with water, dried, and evaporated. The residue was purified by column chromatography on silica gel (chloroform-methanol (50:1)) to give 2-[(3-methoxy-4-propoxypyrid-2-yl)methylthio]benzimidazole (0.35 g) as a light brown oil.

NMR(CDCl$_3$) δ: 1.06(3H, t), 1.87(2H, m), 3.91(3H, s), 3.99(2H, m), 4.41(2H, m), 6.88(1H, d, J=6 Hz), 7.1–7.3(2H, m), 7.45–7.65(2H, m), 8.16(1H, d, J=6 Hz).

EXAMPLE 3

To a suspension of potassium salt of 2-mercaptobenzimidazole (1.3 g) and potassium carbonate (1.0 g) in dimethylformamide (15 ml) was added with stirring, a solution of 2-bromomethyl-4-ethoxy-3-methoxy-pyridine (1.6 g) in dimethylformamide (5 ml), and the mixture was stirred at room temperature for 30 minutes. The reaction mixture was diluted with chloroform (50 ml), washed with water, 1N-sodium hydroxide, and water in this order, dried, and evaporated. The residue was purified by column chromatography on silica gel (chloroform-methanol (50:1)), to give 2-[(4-ethoxy-3-methoxypyrid-2-yl)methylthio]benzimidazole (1.4 g) as a light yellow oil.

NMR(CDCl$_3$) δ: 1.46(3H, t), 3.9(3H, s), 4.12(2H, q), 4.40(2H, s), 6.79(1H, d, J=5 Hz), 7.1–7.3(2H, m), 7.45–7.65(2H, m), 8.19(1H, d, J=5 Hz).

EXAMPLE 4

To a solution of 5-trifluoromethyl-2-mercaptobenzimidazole (1.10 g), 1N-sodium hydroxide (7.2 ml), and methanol (5 ml) was added a solution of 2-bromomethyl-3,4-dimethoxypyridine (1.3 g) in methanol (35 ml) at room temperature over 10 minutes. The mixture was stirred for one hour, concentrated, and extracted with chloroform. The organic layer was washed with 1N-sodium hydroxide and then with water, dried, and evaporated. The residue was purified by column chromatography on silica gel (chloroform-ethyl acetate-acetone (1:1:0.1)) and recrestallized from chloroform-isopropyl ether, to give 2-[(3,4-dimethoxypyrid-2-yl)methylthio]-5-trifluoromethylbenzimidazole (310 mg) as white crystals.

NMR(CDCl$_3$) δ: 3.95(6H, s), 4.43(2H, s), 6.87(1H, d, J=6 Hz), 7.41(1H, dd, J=1.5 and 9 Hz), 7.60(1H, d, J=9 Hz), 7.80(1H, bs), 8.27(1H, d, J=6 Hz).

EXAMPLE 5

In the manner of Example 4, 2-[(3,4-dimethoxypyrid-2-yl)methylthio]-5-methoxybenzimidazole was produced from 5-methoxy-2-mercaptobenzimidazole and 2-bromomethyl-3,4-dimethoxypyridine. The product was resinous.

NMR(CDCl$_3$) δ: 3.77(3H, s), 3.86(6H, s), 4.41(2H, s), 6.75(1H, d, J=6 Hz), 6.78(1H, dd), 7.03(1H, d, J=3 Hz), 7.40(1H, d, J=9 Hz), 8.17(1H, d, J=6 Hz).

EXAMPLE 6

To a solution of 2-[(3,4-dimethoxypyrid-2-yl)methylthio]benzimidazole (1.08 g) in methylene chloride (30 ml) was added m-chloroperbenzoic acid (0.79 g) in small protions below 10° C. After completion of the reaction the reaction, the mixture was diluted with methylene chloride (70 ml), washed with an aqueous solution of potassium carbonate and then with water, dried, and evaporated. The residue was purified by column chromatography on silica gel (chloroform-methanol (40:1)) and crystallized from acetone-ether, to give 2-[(3,4-dimethoxypyrid-2-yl)methylsulfinyl]benzimidazole (670 mg) as light brown crystals. m.p. 149°–151° C. (decomposed).

EXAMPLE 7

In the manner of Example 6, 2-[(3-methoxy-4-propoxypyrid-2-yl)methylsulfinyl]benzimidazole (from acetone-ether-hexane) was obtained as crystals from 2-[(3-methoxy-4-propoxypyrid-2-yl)methylthio]benzimidazole. m.p. 108°–111° C.

EXAMPLE 8

In the manner of Example 6, 2-[(4-ethoxy-3-methoxypyrid-2-yl)methylsulfinyl]benzimidazole was obtained as an amorphous powder from 2-[(4-ethoxy-3-methoxy-prid-2-yl)methylthio]benzimidazole.

NMR(CDCl$_3$) δ: 1.40(3H, t), 3.80(3H, s), 4.03(2H, q), 4.81(2H, s), 6.67(1H, d, J=6 Hz), 7.15–7.35(2H, m), 7.40–7.65(2H, m), 8.08(1H, d, J=6 Hz).

EXAMPLE 9

In the manner of Example 6, 2-[(3,4-dimethoxypyrid-2-yl)methylsulfinyl]-5-trifluoromethylbenzimidazole (from chloroform-ethanol) was obtained as crystals from 2-[(3,4-dimethoxypyrid-2-yl)methylthio]-5-trifluoromethylbenzimidazole. m.p. 158°–161° C. (decomposed).

EXAMPLE 10

In the manner of Example 6, 2-[(3,4-dimethoxypyrid-2-yl)methylsulfinyl]-5-methoxybenzimidazol was obtained as an amorphous powder from 2-[(3,4-dimethoxyprid-2-yl)methylthio]-5-methoxybenzimidazole.

NMR(CDCl$_3$) δ: 3.83 and 3.85(9H), 4.83(2H, s), 6.76(1H, d, J=6 Hz), 6.93(1H, dd, J=2 and 9 Hz), 7.02(1H, d), 7.55(1H, d, J=9 Hz), 8.19(1H, d, J=6 Hz).

EXAMPLE 11

A mixture of 3-methoxy-2-methyl-4-(2,2,2-trifluoroethoxy pyridine (1.1 g) and N-bromosuccinimide (0.89 g) in carbon tetrachloride (100 ml) was refluxed for 2 hours under infrared irradiation. The reaction mixture was washed with water and dried with anhydrous magnesium sulfate. The solvent was evaporated and the residue was dissolved in ether (10 ml) at once. This ether solution was added to a solution of 2-mercapto-5-methoxybenzimidazole (0.90 g) and 2N-sodium hydroxide (2.5 ml) in methanol (20 ml), and stirred at room temperature for 50 minutes. The solvent was evaporated, and the residue was purified by column chromatography and recrystallized from ethyl acetate and hexane, to give 5-methoxy-2-[[3-methoxy-4-(2,2,2-trifluoroethoxy)pyrid-2-yl]methylthio]benzimidazole (989 mg) as yellow crystals. m.p. 149°–150° C.

NMR(CDCl$_3$) δ: 3.82(3H, s), 3.94(3H, s), 4.34(2H, s), 4.45(2H, q, J=8 Hz), 6.79(d, J=6 Hz), 6.79(d like, J=8 Hz), 7.02(1H, d, J=2 Hz), 7.39(1H, d, J=8 Hz), 8.26(1H, d, J=6 Hz).

EXAMPLE 12

A mixture of 3-methoxy-2-methyl-4-(2,2,2-trifluoroethoxy)pyridine (1.1 g) and N-bromosuccinimide (0.89 g) in carbon tetrachloride (100 ml) was refluxed for 2 hours under infrared irradiation. The reaction mixture was washed with water and dried with magnesium sulfate, and evaporated. The residue was dissolved in ether (10 ml) at once. This ether solution was added to a solution of 2-mercapto-5-trifluoromethylbenzimidazole (654 mg), methanol (10 ml) and 2N-sodium hydroxide (1.5 ml), and stirred at room temperature for one hour. The solvent was evaporated, and the residue was purified on a silica gel column, and recrystallized from chloroform to give 2-[[(3-methoxy-4-(2,2,2-trifluoroethoxy)pyrid-2-yl]methylthio]-5-trifluoromethylbenzimidazole (690 mg) as white crystals. m.p. 80°–82° C.

NMR(CDCl$_3$) δ: 3.98(3H, s), 4.45(2H, s), 4.50(2H, q, J=8 Hz), 6.86(1H, d, J=5.5 Hz), 7.44(1H, dd, J=2 and 9 Hz), 7.63(1H, d, J=9 Hz), 7.83(1H, s like), ca 8.0(1H, br), 8.30(1H, d, J=5.5 Hz).

EXAMPLE 13

By the reaction of Example 12, 2-[[-3-methoxy-4-(2,2,2-trifluoroethoxy)pyrid-2-yl]methylthio]benzimidazole was obtained as crystals from 3-methoxy-2-methyl-4-(2,2,2-trifluoroethoxy)pyridine and 2-mercaptobenzimidazole. m.p. 113°–115° C.

NMR(CDCl$_3$) δ: 3.97(3H, s), 4.43(2H, s), 4.46(2H, q, J=8 Hz), 6.81(1H, d, J=6 Hz), 7.09–7.30(2H, m), 7.46–7.63(2H, m), 8.29(1H, d, J=6 Hz).

EXAMPLE 14

3-Methoxy-2-methyl-4-(2,2,3,3,3-pentafluoropropoxy)pyridine (0.85 g) and N-bromosuccinimide (638 mg) in carbon tetrachloride (70 ml) was refluxed for 2 hours under infrared irradiation. The reaction mixture was washed with a saturated saline and dried with magnesium sulfate. The solvent was evaporated, and the residue was dissolved in either (6 ml) at once and added to a solution of 2-mercaptobenzimidazole (576 mg) and 2N-NaOH (1.9 ml) in methanol (15 ml). The mixture was stirred at room temperature for 15 minutes, evaporated, treated with water, and extracted with ethyl acetate. The extract was washed with about 0.5N-sodium hydroxide in water, dried with magnesium sulfate, and evaporated. The residue was purified by column chromatography and recrystallized from isopropyl ether-ethyl acetate, to give 2-[[3-methoxy-4-(2,2,3,3,3-pentafluoropropoxy)pyrid-2-yl]methylthio]benzimidazole (710 mg) as white crystals. m.p. 116.5°–117.0° C.

NMR(CDCl$_3$) δ: 3.93(3H, s), 4.41(2H, s), 4.52(2H, t, J=12 Hz), 6.81(1H, d, J=5.5 Hz), 7.05–7.3 (2H, m), 7.35–7.7 (2H, m), 8.27(1H, d, J=5.5 Hz), 12.52(br, s).

EXAMPLE 15

In this manner of Example 14, 2-[[3-methoxy-4-(2,2,3,3,3-pentafluoropropoxy)pyrid-2-yl]methylthio]-5-trifluoromethylbenzimidazole (recrystallized from isopropyl ether) was obtained as crystals from 2-mercapto-5-trifluoromethylbenzimidazole and 3-methoxy-2-methyl-4-(2,2,3,3-pentafluoropropoxy)pyridine. m.p. 127°–128° C.

NMR(CDCl$_3$) δ: 3.95(3H, s), 4.42(2H, s), 4.53(2t, J=12 Hz), 6.89(1H, d, J=5.5 Hz), 7.40(1H, dd, J=8 and 1.5 Hz), 7.59(1H, d, J=8 Hz), 7.80(1H, s like), 8.29(1H, d, J=5.5 Hz).

EXAMPLE 16

5-Methoxy-2-[[3-methoxy-4-(2,2,2-trifluoroethoxy)-pyrid-2-yl]methylthio]benzimidazole (989 mg) was dissolved in chloroform (30 ml), to which a solution of m-chloroperbenzoic acid (503 mg) in chloroform (8 ml) was added dropwise under ice-cooling over 5 minutes. The reaction mixture was washed with a saturated aqueous solution of sodium bicarbonate and then a saturated saline, and dried with anhydrous magnesium sulfate. The solvent was evaporated and the residue was purified by column chromatography, to give 5-methoxy-2-[[3-methoxy-4-(2,2,2-trifluoroethoxy)pyrid-2-yl]methylsulfinyl]benzimidazole (712 mg) as a light brownish yellow powder. m.p. 36°–46° C.

NMR(CDCl$_3$) δ: 3.82(6H, s), 4.33(2H, q, J=8 Hz), 4.82(2H, s), 6.70(1H, d, J=6 Hz), 6.85–7.15(1H, br), 6.92(1H, dd, J=9 and 2 Hz), 7.86(1H, br), 8.12(1H, d, J=6 Hz), 12.47(br, s).

EXAMPLE 17

In the manner of Example 16, 2-[[3-methoxy-4-(2,2,2-trifluoroethoxy)pyrid-2-yl]methylsulfinyl]-5-trifluoromethylbenzimidazole (recrystallized from ethyl acetate-hexane) was obtained as white crystals from 2-[[3-methoxy-4-(2,2,2-trifluoroethoxy)pyrid-2-yl]methylthio]-5-trifluoromethylbenzimidazole. m.p. 147°–149° C. (decomp.).

NMR(CDCl$_3$) δ: 3.80(3H, s), 4.31(2H, q, J=8 Hz), 4.88(2H, s like), 6.69(1H, d, J=5.5 Hz), 7.38–7.98(3H, m), 8.07(1H, d, J=5.5 Hz).

EXAMPLE 18

In the manner of Example 16, 2-[[3-methoxy-4-(2,2,2-trifluoroethoxy)pyrid-2-yl]methylsulfinyl]benzimidazole was obtianed from 2-[[3-methoxy-4-(2,2,2-trifluoroethoxy)pyrid-2-yl]methylthio]benzimidazole.

NMR(CDCl$_3$) δ: 3.82(3H, s), 4.31(2H, q, J=8 Hz), 4.88(2H, s), 6.70(1H, d, J=6 Hz), 7.20–7.40(2H, m), 7.49–7.73(2H, m), 8.14(1H, d, J=6 Hz).

EXAMPLE 19

In the manner of Example 16, 2-[[3-methoxy-4-(2,2,3,3,3-pentafluoropropoxy)pyrid-2-yl]methylsulfinyl]benzimidazole 1/4H$_2$O was obtained as a white powder from 2-[[3-methoxy-4-(2,2,3,3,3-pentafluoropropoxy)pyrid-2-yl]methylthio]benzimidazole. m.p. 59°–65° C.

NMR(CDCl$_3$) δ: 3.79(3H, s), 4.37(2H, t, J=12 Hz), 4.83(2H, s like), 6.69(1H, d, J=5.5 Hz), 7.27 (2H, m), 7.57(2H, m), 8.10(1H, d, J=5.5 Hz).

EXAMPLE 20

In the manner of Example 16, 2-[[3-methoxy-4-(2,2,3,3,3-pentafluoropropoxy)pyrid-2-yl]methylsulfinyl]-5-trifluoromethylbenzimidazole was obtained as a pale brownish yellow powder from 2-[[3-methoxy-4-(2,2,3,3,3-pentafluoropropoxy)pyrid-2-yl]methylthio]-5-trifluoromethylbenzimidazole. m.p. 52°–56° C.

NMR(CDCl$_3$) δ: 3.83(3H, s), 4.39(2H, t, J=12 Hz), 4.79(1H, d, J=14 Hz), 4.87(1H, d, J=14 Hz), 6.74(1H, d, J=5.5 Hz), 7.4–8.1(3H, m), 8.13(1H, d, J=5.5 Hz).

EXAMPLE 21

| Tablet | |
|---|---|
| (1) Compound A* | 50 mg |
| (2) Corn starch | 20 mg |
| (3) Lactose | 65.2 mg |
| (4) Micro crystalline cellulose | 60 mg |
| (5) Light anhydrous silicic acid | 1.8 mg |
| (6) Magnesium stearate | 3.0 mg |
| | 200 mg (One tablet) |

*Compound A was produced in Example 6.

(Production method)

The above ingredients (1), (2) and (3) were mixed and then mixed with the half amount of the above ingredients (4), (5) and (6). The blended mixture was compressed and formed using a drying-granulator (Roller Compactor, Freund Industrial, Co., Ltd., Japan). After this slug was comminuted in a mortar and sieved by a 16-mesh sieve, to the granule obtained was added the remaining amount of the ingredients (4), (5) and (6) and mixed together. Then, the mixture was compressed using a rotary-tableting machine (Kikusui Seisakusho Ltd., Japan) to obtain tablets (200 mg per one tablet).

EXAMPLE 22

| Capsule | |
|---|---|
| (1) Compound B* | 30 mg |
| (2) Corn starch | 40 mg |
| (3) Lactose | 74 mg |
| (4) Hydroxypropylcellulose | 6 mg |
| (5) Water | (0.1 ml) |
| | 150 mg (One capsule) |

*Compound B was produced in Example 9.

(Production methods)

The above ingredients (1) to (4) were mixed together. To the resulting mixture was added water. The mixture, after being kneaded, was dried at vacuum at 40° C. for 16 hours. The dried mass was comminuted in a mortar and sieved by a 16-mesh sieve to obtain granules. By filling these granules in a gelatin capsule (No. 3), a capsule was produced.

EXAMPLE 23

| Granules | |
|---|---|
| (1) Compound C* | 30 mg |
| (2) Corn starch | 80 mg |
| (3) Micro crystalline cellulose | 20 mg |
| (4) Carboxymethylcellulose calcium | 10 mg |
| (5) Hydroxypropylcellulose | 10 mg |
| (6) Pluronic F-68 (Asahi Denka Kogyo, Japan) | 4 mg |
| (7) Lactose | 46 mg |
| (8) Water | (0.1 ml) |
| | 200 mg |

*Compound C was produced in Example 18.

(Production method)

The above ingredients (1) to (7) were mixed together. To the resulting mixture was added water. Then, the mixture was kneaded. The wet mass was extruded using an extruder (Kikusui Seisakusho Ltd., Japan, screen diameter: 1.0 mm). Upon producing spherical granules using a spheronizer (Marumerizer, Fuji Paudal Ltd., Japan), the granules obtained were dried at vacuum at 40° C. for 16 hours and then sieved by a sieve to obtain 12–42 mesh granules.

What we claim is:

1. A compound of the formula

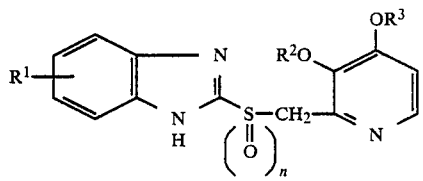

wherein $R^1$ is hydrogen, fluorine, methoxy or trifluoromethyl, $R^2$ is a $C_{1-8}$ alkyl, $R^3$ is a $C_{1-8}$ alkyl which may be fluorinated, and n is 0 or 1, or a pharmacologically acceptable salt thereof.

2. A compound according to claim 1, wherein $R^1$ is hydrogen.

3. A compound according to claim 1, wherein $R^1$ is fluorine.

4. A compound according to claim 1, wherein $R^1$ is methoxy.

5. A compound according to claim 1, wherein $R^1$ is trifluoromethyl.

6. A compound according to claim 1, wherein $R^2$ is a $C_{1-4}$ alkyl.

7. A compound according to claim 1, wherein $R^2$ is methyl.

8. A compound according to claim 1, wherein $R^3$ is a $C_{1-4}$ alkyl.

9. A compound according to claim 1, wherein $R^3$ is a $C_{2-4}$ fluorinated alkyl.

10. A compound according to claim 1, wherein $R^3$ is methyl.

11. A compound according to claim 1, wherein $R^3$ is ethyl.

12. A compound according to claim 1, wherein $R^3$ is propyl.

13. A compound according to claim 1, wherein $R^3$ is 2,2,2-trifluoroethyl.

14. A compound according to claim 1, wherein $R^3$ is 2,2,3,3,3-pentafluoropropyl.

15. A compound according to claim 1, wherein $R^3$ is 2,2,3,3-tetrafluoropropyl.

16. A compound according to claim 1, wherein the compound is 2-[(3,4-dimethoxypyrid-2-yl)methylthio]-benzimidazole.

17. A compound according to claim 1, wherein the compound is 2-[(3-methoxy-4-propoxypyrid-2-yl)methylthio]benzimidazole.

18. A compound according to claim 1, wherein the compound is 2-[(3-methoxy-4-ethoxypyrid-2-yl)methylthio]benzimidazole.

19. A compound according to claim 1, wherein the compound is 2-[(3,4-dimethoxypyrid-2-yl)methylthio]-5-trifluoromethylbenzimidazole.

20. A compound according to claim 1, wherein the compound is 2-[(3,4-dimethoxypyrid-2-yl)methylthio]-5-methoxybenzimidazole.

21. A compound according to claim 1, wherein the compound is 2-[(3,4-dimethoxypyrid-2-yl)methylsulfinyl]benzimidazole.

22. A compound according to claim 1, wherein the compound is 2-[(3-methoxy-4-propoxypyrid-2-yl)methylsulfinyl]benzimidazole.

23. A compound according to claim 1, wherein the compound is 2-[(3-methoxy-4-ethoxypyrid-2-yl)methylsulfinyl]benzimidazole.

24. A compound according to claim 1, wherein the compound is 2-[(3,4-dimethoxypyrid-2-yl)methylsulfinyl]-5-trifluoromethylbenzimidazole.

25. A compound according to claim 1, wherein the compound is 2-[(3,4-dimethoxypyrid-2-yl)methylsulfinyl]-5-methoxybenzimidazole.

26. A compound according to claim 1, wherein the compound is 5-methoxy-2-[[3-methoxy-4-(2,2,2-trifluoroethoxy)pyrid-2-yl]methylthio]benzimidazole.

27. A compound according to claim 1, wherein the compound is 2-[[3-methoxy-4-(2,2,2-trifluoroethoxy)pyrid-2-yl]methylthio]5-fluoromethylbenzimidazole.

28. A compound according to claim 1, wherein the compound is 2-[[3-methoxy-4-(2,2,2-trifluoroethoxy)pyrid-2-yl]methylthio]benzimidazole.

29. A compound according to claim 1, wherein the compound is 2-[[3-methoxy-4-(2,2,3,3,3-pentafluoropropoxy)pyrid-2-yl]methylthio]benzimidazole.

30. A compound according to claim 1, wherein the compound is 2-[[3-methoxy-4-(2,2,3,3,3-pentafluoropropoxy)pyrid-2-yl]methylthio]-5-trifluoromethylbenzimidazole.

31. A compound according to claim 1, wherein the compound is 5-methoxy-2-[[3-methoxy-4-(2,2,2-trifluoroethoxy)pyrid-2-yl]methylthio]benzimidazole.

32. A compound according to claim 1, wherein the compound is 2-[[3-methoxy-4-(2,2,2-trifluoroethoxy)pyrid-2-yl]methylsulfinyl]benzimidazole.

33. A compound according to claim 1, wherein the compound is 2-[[3-methoxy-4-(2,2,2-trifluoroethoxy)pyrid-2-yl]methylsulfinyl]benzimidazole.

34. A compound according to claim 1, wherein the compound is 2-[[3-methoxy-4-(2,2,3,3,3-pentafluoropropoxy)pyrid-2-yl]methylsulfinyl]benzimidazole.

35. A compound according to claim 1, wherein the compound is 2-[[3-methoxy-4-(2,2,3,3,3-pentafluoropropoxy)pyrid-2-yl]methylsulfinyl-5-trifluoromethylbenzimidazole.

36. A anti-ulcer composition for preventing or treating digestive ulcers, which contains an anti-ulceratively effective amount of a compound of the formula

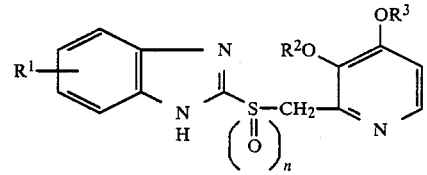

wherein $R^1$ is hydrogen, fluorine, methoxy or trifluoromethyl, $R^2$ is a $C_{1-8}$ alkyl, $R^3$ is a $C_{1-8}$ alkyl which may be fluorinated, and n is 0 or 1, or a pharmacologically acceptable salt thereof and carriers.

* * * * *